(12) United States Patent
Maier et al.

(10) Patent No.: US 12,298,368 B2
(45) Date of Patent: May 13, 2025

(54) DEVICE AND METHOD FOR REAL-TIME 3D DISTORTION CORRECTION OF MAGNETIC RESONANCE IMAGES

(71) Applicant: Siemens Healthcare GmbH, Erlangen (DE)

(72) Inventors: Florian Maier, Buckenhof (DE); Martin Requardt, Nuremberg (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 18/525,054

(22) Filed: Nov. 30, 2023

(65) Prior Publication Data

US 2024/0210500 A1 Jun. 27, 2024

(30) Foreign Application Priority Data

Dec. 27, 2022 (EP) .................................... 22216784

(51) Int. Cl.
| | |
|---|---|
| *G01V 3/00* | (2006.01) |
| *A61B 90/00* | (2016.01) |
| *G01R 33/28* | (2006.01) |
| *G01R 33/483* | (2006.01) |
| *G01R 33/56* | (2006.01) |

(52) U.S. Cl.
CPC ............ *G01R 33/287* (2013.01); *A61B 90/37* (2016.02); *G01R 33/4835* (2013.01); *G01R 33/5608* (2013.01); *A61B 2090/374* (2016.02)

(58) Field of Classification Search
CPC .............. G01R 33/287; G01R 33/4835; G01R 33/5608; A61B 2090/374

USPC ........................................................ 324/309
See application file for complete search history.

(56) References Cited

U.S. PATENT DOCUMENTS

| | | | |
|---|---|---|---|
| 9,848,799 B2 | 12/2017 | Govari et al. | |
| 2015/0374260 A1 | 12/2015 | Govari et al. | |
| 2020/0085381 A1 | 3/2020 | Weine | |

FOREIGN PATENT DOCUMENTS

| | | | | |
|---|---|---|---|---|
| EP | 3799063 A1 | 3/2021 | | |
| EP | 4253977 A1 | 10/2023 | | |
| WO | WO-2012172474 A1 | * | 12/2012 | ......... A61B 1/00149 |

OTHER PUBLICATIONS

European Intention to Grant Application EP 22 216 784.3-1122, mailed on Sep. 30, 2024, with English translation.

(Continued)

*Primary Examiner* — Walter L Lindsay, Jr.
*Assistant Examiner* — Frederick Wenderoth
(74) *Attorney, Agent, or Firm* — Lempia Summerfield Katz LLC

(57) ABSTRACT

A magnetic resonance tomography device and a method for equalized mapping in real time are provided. A first slice and a second slice are captured in three-dimensional (3D) encoding, where the first slice and the second slice are oriented to one another at an angle, and an instrument or trajectory to be mapped lies in an intersecting set of both the first slice and the second slice. A two-dimensional (2D) image may be generated alternately from both the first slice and the second slice and is displayed to a user.

15 Claims, 3 Drawing Sheets

(56) References Cited

OTHER PUBLICATIONS

European Search Report for European App. 22 216 784.3-1122, mailed on May 30, 2023, with English translation.
Elgort et al.; "A Review of Technical Advances in Interventional Magnetic Resonance Imaging"; Academic Radiology, vol. 12, No. 9, Sep. 2005; pp. 1089-1099.
Heidt et al.; "Real-time magnetic resonance imaging—guided coronary intervention in a porcine model", Scientific Reports, vol. 9, Jun. 2019; pp. 1-10.

* cited by examiner

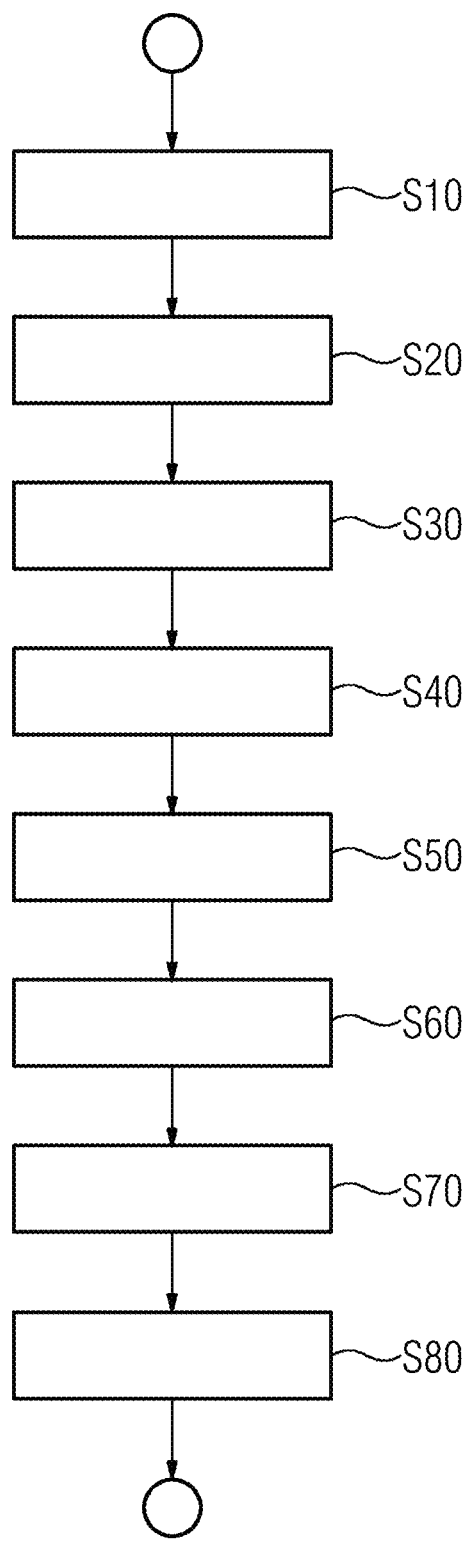

DEVICE AND METHOD FOR REAL-TIME 3D DISTORTION CORRECTION OF MAGNETIC RESONANCE IMAGES

This application claims the benefit of European Patent Application No. EP 22216784.3, filed on Dec. 27, 2022, which is hereby incorporated by reference in its entirety.

BACKGROUND

The present embodiments relate to a magnetic resonance tomography device and a method for real-time tracking of a medical instrument in the context of interventional magnetic resonance (MR) imaging.

In minimally invasive medical procedures, medical instruments (e.g., catheters and/or intervention needles) are inserted into a patient, with image monitoring of the procedure normally taking place. The image monitoring enables images in which the medical instrument is made visible in relation to its anatomical surroundings to be acquired. Whereas traditionally X-ray imaging has been used for image monitoring of minimally invasive medical interventions, (e.g., fluoroscopy), it has now also been proposed to employ magnetic resonance devices, and consequently magnetic resonance (MR) imaging, for image monitoring. This is typically referred to as interventional MR imaging.

In this case, most medical instruments are made of metal or of other materials not directly to be mapped with the magnetic resonance acquisition of the protons in the water or fat of the body. Instead, indirect methods are used for the mapping, in which indirect effects or artifacts are used for mapping. For real-time tracking, short repetition periods are necessary, but this only provides poor image quality. In addition, in magnetic resonance tomography, geometrical distortions are normal, which, in contrast to geometrically faithful mapping using X-rays, make it harder to track the thin instruments.

SUMMARY AND DESCRIPTION

The scope of the present invention is defined solely by the appended claims and is not affected to any degree by the statements within this summary.

The present embodiments may obviate one or more of the drawbacks or limitations in the related art. For example, tracking of a medical instrument during an intervention is improved.

The magnetic resonance tomography device of the present embodiments is configured to map a medical instrument on a trajectory in real time. The magnetic resonance tomography device has a controller that coordinates the activities necessary for image acquisition with the magnetic resonance tomography device. The controller may, in this case, also be divided into subunits. For example, the controller may divided into a gradient controller and a radio-frequency controller for controlling procedures in real time, an operating interface for interaction with an operator, and an image reconstruction computer with high computing capacity.

The controller is configured to actuate the magnetic resonance tomography device so that a first slice is captured by 3D encoding. In this case, a 3-dimensional volume is regarded as a slice (e.g., a "slab") that also has a thickness for the purpose of magnetic resonance mapping (e.g., consists not just of a single two-dimensional arrangement of voxels of the magnetic resonance mapping in a plane, but of at least two layers of voxels above one another, such as multiple layers). Thus, it is possible for the medical instrument to be captured in full despite distortions in the image.

The controller is in this case configured to select a position of the first slice as a function of the trajectory and the slice thickness as a function of a predetermined distortion of the magnetic resonance tomography device during mapping or to set parameters for the capture of the first slice, such that the trajectory or the medical instrument is captured in full by the first slice. In this connection, the position includes both the location and orientation of the slice. The trajectory may, for example, be specified by the intervention, by coordinates that were ascertained during the planning. In one embodiment, the trajectory may be determined beforehand (e.g., by the position and/or orientation of the medical instrument being captured by an image). With knowledge of the position of the trajectory and the distortions of the image by the magnetic resonance tomography device, the controller may ascertain a volume (e.g., a cuboid of voxels), in which the trajectory is situated, taking account of the distortion. The slice thickness in this case may be configured, so that the slice only includes the trajectory (e.g., contains few if any layers of voxels that are not penetrated by the trajectory or do not contain any voxels associated with the trajectory) in order to accelerate the 3D encoding.

The controller is further configured to capture a second slice in the described manner using 3D encoding, where the controller selects a position of the second slice as a function of the trajectory and the slice thickness as a function of a predetermined distortion of the magnetic resonance tomography device during imaging, so that the trajectory is captured in full by the second slice.

The controller is also configured to select the positions of the first slice and the second slice, such that the first slice and the second slice confine an angle greater than 20 degrees, 40 degrees or 60 degrees, less than or equal to 90 degrees, and the trajectory of the medical instrument and/or the medical instrument is situated in an intersecting set or intersecting volume of the first slice and the second slice. In one embodiment, the controller may rotate the coordinates of the first slice through the angle about the trajectory, in order to obtain the position of the second slice.

The respective slice also supplies an image of the wider surrounding area of the trajectory in the direction of lateral or flat extension. In this case, the extension of the slice may correspond in each case to the orientation of the two-dimensional images that are subsequently displayed to the user for navigation, so that the wider surrounding area may also be displayed for orientation. By displaying images from both slices (e.g., by combining image data of both slices), it is possible to achieve a high repeat rate for the trajectory and at the same time to display a wider surrounding area.

The controller is configured to generate a sequence of two-dimensional images of the medical instrument in a predetermined plane. The trajectory and thus the medical device lie in this plane. The images are generated from the first slice and the second slice, or in the case of a repetition, from a plurality of first slices and second slices. The predetermined plane may be parallel to the first slice or the second slice, but may also confine a small angle with the first slice or the second slice, in order to be able to reproduce as much as possible of the surrounding area of the trajectory. A further image may also be generated and displayed by the controller. The further image has a plane of representation that lies parallel to or at a small angle to the other slice and thus enables display of the trajectory or tracking of the medical instrument from different perspectives.

The controller is also configured finally to output the sequence of two-dimensional images to a user (e.g., on a screen). The output in this case takes place as immediately as possible after the generation of the image, in order to provide that the medical instrument or the trajectory is displayed in real time or virtually real time. For example, the acquisition of a first slice, generation of the two-dimensional image in the plane, and the output thereof may take place before or while the second slice is acquired and the two-dimensional image is generated.

In one embodiment, two-dimensional images are in each case generated and displayed alternately from acquisitions of the first slice and the second slice, in order to generate the trajectory from different perspectives or lines of sight substantially perpendicular to the respective slice. In this case, the region of the images corresponding to the intersecting set or intersecting volume of both the slices may be respectively updated or displayed with the capture of the first slice and the second slice.

The acquisition of both the slices, oriented at an angle to one another, with the trajectory inside the slices, may enable deviations of the movement of the medical instrument from the trajectory in space to be quickly captured and displayed to the user, including the wider surrounding area. For example, the image repetition rate for the trajectory in the intersecting set of the slices doubles in comparison to a magnetic resonance tomography device that alternately acquires slices arranged at an angle to one another, in order to track a movement three-dimensionally, but then only in each case generates the two-dimensional image from the slice that is oriented substantially parallel to the display plane. The region of the intersecting set of both slices with the trajectory may therefore also be updated with each capture of one of the two slices in the image that is oriented in parallel to the other slice, and thus, the image repetition rate for this region is doubled.

The method of the present embodiments shares the advantages of the device of the present embodiments.

In one possible embodiment of the magnetic resonance tomography device, the controller of the magnetic resonance tomography device is configured to perform an equalization of the predetermined distortion of the first slice and/or the second slice. The distortion of an image capture of the magnetic resonance tomography device may be caused by inhomogeneities in the static magnetic field, the gradient fields, and dynamically by eddy currents, and is to this extent predetermined by the magnetic resonance tomography device. The predetermined distortion may in this case be ascertained type-specifically for the magnetic resonance tomography device by calculation during the development or test scans. In one embodiment, the predetermined distortion may be determined by calibration measurements individually for single devices during installation or prior to an image capture. For the determined distortion as a linear mapping, for example, defined by a matrix, there is a corresponding inverse function that may be determined from the predetermined distortion through the medium of linear algebra, in order to equalize the captured first slice and/or second slice, such that the trajectory or the medical device is displayed geometrically correctly (e.g., reproduces this as a section of a straight line in the case of a straight or linear trajectory).

In one embodiment, thanks to the equalization, the geometry of the detected 3D data and thus also of the 2-dimensional image generated therefrom is corrected, so that the user is offered an undistorted display of the medical instrument and of the trajectory, and thus, the intuitive navigation of the instrument is facilitated.

In one embodiment of the magnetic resonance tomography device, the magnetic resonance tomography device is further configured to perform averaging of the first slice and/or second slice after the equalization. Averaging may provide that by averaging across multiple adjacent voxels of the 3D magnetic resonance acquisition, a signal-to-noise ratio (SNR) of the image capture is improved. In the simplest case and original meaning of the word, averaging is a binning, a combination of adjacent voxels to form virtual, larger voxels by summing the values. However, at the same time, the spatial resolution diminishes. However, with the reduced resolution, a result of the equalization, for example, becomes significantly worse. Other forms of averaging may, however, be provided, for example, with a weighted summation.

In one possible embodiment of the magnetic resonance tomography device, the controller is therefore further configured to perform the equalization with a resolution greater than a resolution of the subsequent two-dimensional image.

The equalization may therefore take place in the magnetic resonance tomography device of the present embodiments before the resolution is reduced by averaging or binning, so that a location of the medical instrument may be displayed more accurately. Averaging takes place only afterwards, in order to improve the SNR of the corrected acquisition. Since the averaging itself is not a reversible mapping or function, the order is crucial and changes the result. With a higher resolution of the magnetic resonance data, this data may be equalized with a better result. The impaired SNR that is achieved with the higher resolution with an identical scan time may then be improved again by the downstream averaging.

In one embodiment of the magnetic resonance tomography device, the controller is further configured to capture a third slice containing the medical instrument with 3D encoding. The third slice may be captured with a higher resolution and/or longer integration time than the first slice and/or second slice, so that, for example, the surrounding area of the medical instrument may be captured and displayed more accurately. The controller is in this case configured to generate the images as a function of the third slice during the generation of the sequence of two-dimensional images. In one embodiment, in this case, the acquisition of the third slice is used to reproduce a surrounding area of the trajectory with a higher resolution and/or better SNR in the 2-dimensional mapping. The surrounding area of the trajectory hardly changes during the manipulation of the medical instrument, so that data of the acquisition of the third slice may be used for the reproduction of the surrounding area in the 2-dimensional image (e.g., also in multiple consecutive images) without in between repeating or updating the acquisition of the third slice. In one embodiment, segmentation may, for example, be used to capture the location of individual organs or vessels in the first slice and/or second slice and accordingly to correct the location in the acquisition in the third slice for the 2-dimensional image.

Combining an image capture of the surrounding area with a high image quality, but low repetition rate, with fast acquisitions of the first slice and the second slice with the medical instrument may enable the instrument to be tracked in real time with a high resolution of surrounding organs.

In one possible embodiment of the magnetic resonance tomography device, the trajectory captured with the first slice and the second slice is a curved trajectory, or the medical instrument is not configured as substantially linear, but as curved. As already set out for a distortion by the image capture of the magnetic resonance tomography device, by suitably selecting the first slice and the second slice, a linear instrument distorted by the magnetic resonance image may not only be captured in full, but with knowledge of the geometry and location of the trajectory or of the medical instrument, a curved instrument or a curved trajectory may also be captured in full. The cuboid delimiting the first slice and/or second slice is selected so that the cuboid fully encloses the curved instrument or the curved trajectory, taking into consideration the distortions of the magnetic resonance tomography device.

The magnetic resonance tomography device of the present embodiments and the method of the present embodiments are advantageously thus also able to track a curved medical instrument or a corresponding instrument on a curved trajectory in real time.

In one form of embodiment of the magnetic resonance tomography device, the controller is configured to perform a linearization of the curved trajectory during the generation of the two-dimensional image. In one embodiment, the linearization may correct or linearize the distortion by the magnetic resonance tomography device and/or the geometric curvature of the trajectory or of the medical instrument. The correction may in this case take place in a plane or else in space. In one embodiment, for example, a linearization may take place in a plane perpendicular to the plane of the 2-dimensional image.

The magnetic resonance tomography device of the present embodiments and the method of the present embodiments may also enable curved medical instruments or curvable medical instruments on a curved trajectory in a 2-dimensional image to be displayed quickly and in full to a user, and navigation with the medical instrument may be improved.

Independent of the grammatical term usage, individuals with male, female or other gender identities are included within the term.

BRIEF DESCRIPTION OF THE DRAWINGS

The properties, features and advantages of this invention described above and the way these are achieved will be explained more clearly and explicitly in connection with the following description of the embodiments THAT are explained in greater detail in connection with the drawings, in which:

FIG. 5 shows a schematic flow chart of an embodiment of a method.

DETAILED DESCRIPTION

Figure 1:
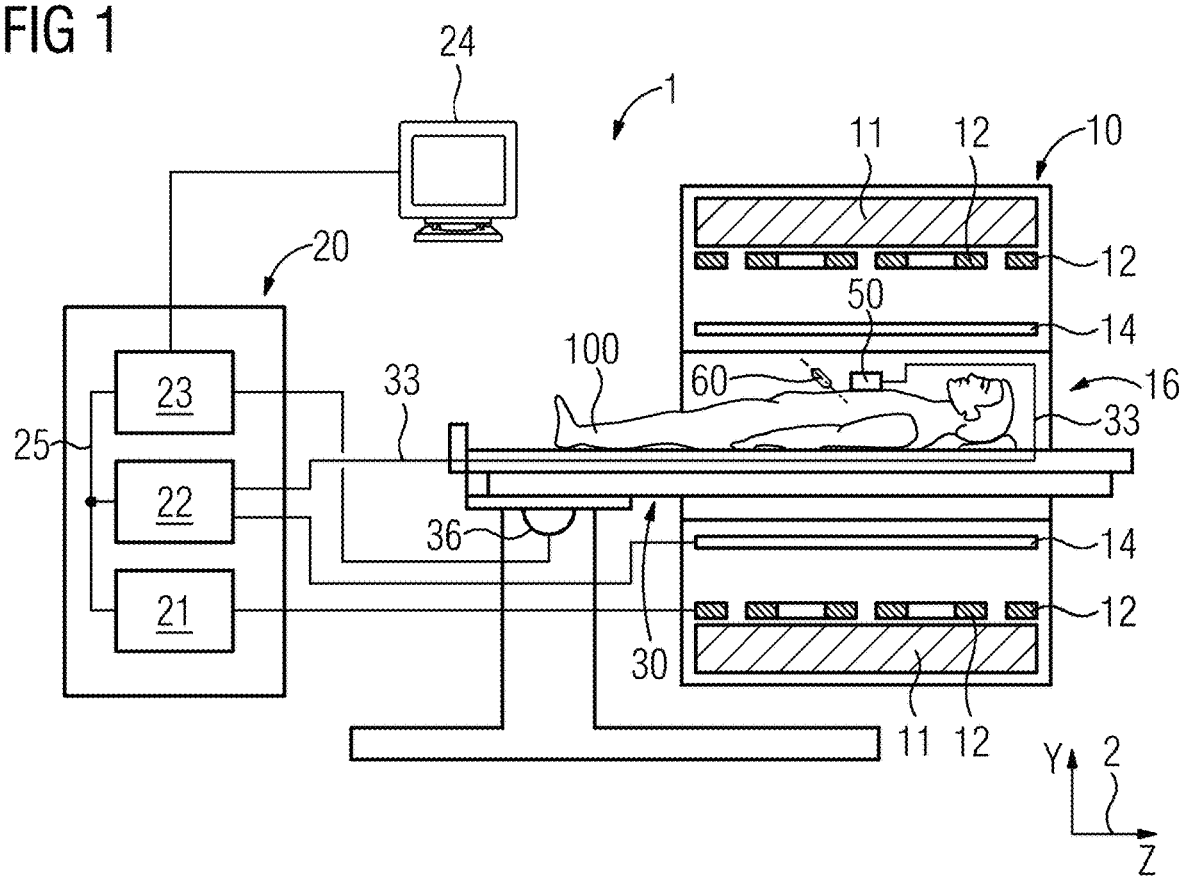
FIG. 1 shows a schematic representation of an embodiment of a magnetic resonance tomography device with an embodiment of an instrument.

FIG. 1 shows a schematic representation of an embodiment of an magnetic resonance tomography device 1, as is also used for the execution of a method of the present embodiments.

The magnet unit 10 has a field magnet 11 that generates a static magnetic field B0 for an orientation of nuclear spins of samples or of a patient 100 in an acquisition region. The acquisition region is characterized by an extremely homogeneous static magnetic field B0, where the homogeneity, for example, relates to the magnetic field strength or the absolute value. The acquisition region is almost spherical and is arranged in a patient tunnel 16 that extends in a longitudinal direction 2 through the magnet unit 10. A patient couch 30 may be moved in a patient tunnel 16 by a positioning unit 36. The field magnet 11 may be a superconducting magnet that may provide magnetic fields with a magnetic flux density of up to 3 T, and even more in the most recent devices. However, permanent magnets or electromagnets with normally conducting coils may also be used for lower magnetic field strengths.

The magnet unit 10 further has gradient coils 12 that are configured, for spatial differentiation of the captured image regions in the examination volume, to superimpose the magnetic field B0 with temporally and spatially variable magnetic fields in three spatial directions. The gradient coils 12 may be coils made of normally conducting wires that may generate fields orthogonal to one another in the examination volume.

The magnet unit 10 likewise has a body coil 14 that is configured to emit a radio-frequency signal fed via a signal line into the examination volume and to receive resonance signals emitted by the patient 100, and to deliver the resonance signals via a signal line.

A control unit 20 supplies the magnet unit 10 with various signals for the gradient coils 12 and the body coil 14 and evaluates the received signals.

Thus, the control unit 20 has a gradient actuator 21 that is configured to supply the gradient coils 12 via feed lines with variable currents that provide the desired gradient fields in the examination volume on a temporally coordinated basis.

The control unit 20 further has a radio-frequency unit 22 that is configured to generate a radio-frequency pulse with a specified temporal profile, amplitude, and spectral power distribution for the excitation of a magnetic resonance of the nuclear spins in the patient 100. In this case, pulse powers in the kilowatt range may be achieved. The excitation signals may be emitted into the patient 100 via the body coil 14 or else via a local transmission antenna.

A controller 23 communicates via a signal bus 25 with the gradient controller 21 and the radio-frequency unit 22.

A medical instrument 60 (e.g., a biopsy needle) is arranged on a patient 100 in a patient tunnel 16 or is inserted into the patient 100 in connection with an intervention and is captured by the magnetic resonance tomography device of the present embodiments and displayed to a user on an output unit such as a screen 24.

Both the static B0 magnetic field of the field magnet 11 and the gradient fields of the gradient coils 12 have inhomogeneities or nonlinearities that result in spatial distortions during the mapping.

Figure 2:
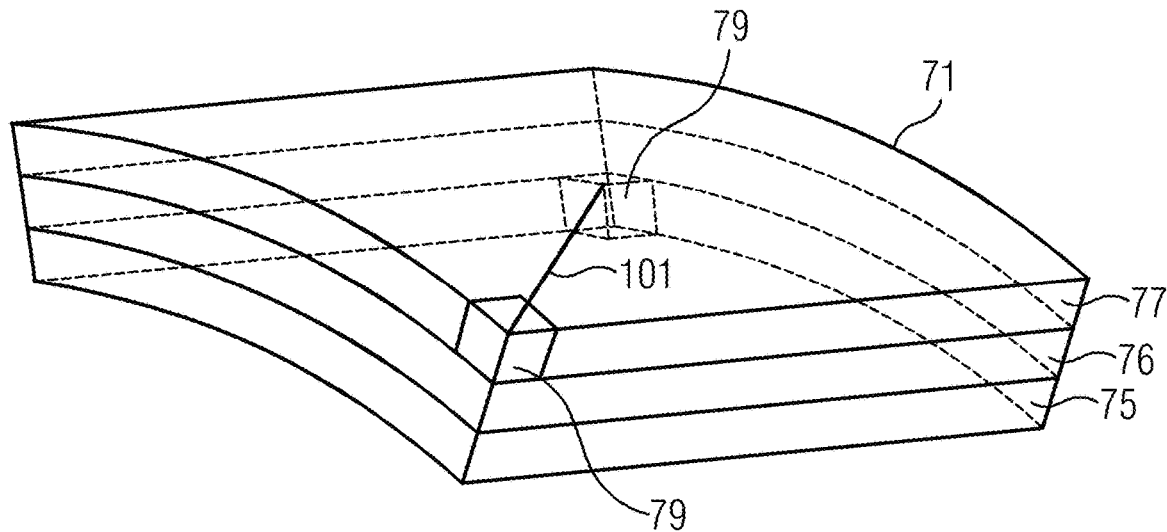
FIG. 2 shows a schematic representation of a slice captured by the magnetic resonance tomography device in an embodiment of a method.

FIG. 2 schematically shows a first slice 71 of an example of an image capture with a registered trajectory 101. FIG. 2 shows the real undistorted geometry (e.g., a medical instrument 60 such as a biopsy needle that geometrically substantially represents a partial straight line is also shown as a partial straight line without curvature). In contrast, the first slice 71 of an image capture by the magnetic resonance tomography device 1 is, due to the distortions of the magnetic resonance image, not a cuboid with straight edges, but is curved or bent.

The distortions that an image experiences due to the magnetic resonance tomography device 1 are substantially determined by the magnetic resonance tomography device 1 and the sequence used. The distortions may thus be determined for the individual magnetic resonance tomography device 1 for a device series of the same type and with higher accuracy for an individual device and a predetermined sequence by calibration measurements. This may be done, for example, by mapping a phantom with a grid composed of magnetic-resonance-active samples with the magnetic resonance tomography device 1 and the corresponding sequence. In one embodiment, a distortion is estimated using a simulation.

The determined distortion supplies a mapping of individual pixels of an examination object in the real geometry to corresponding voxels in a 3D image. A corresponding inverse mapping may be determined through the medium of linear algebra.

For a specified trajectory 101, it is thus possible to determine the locations of the individual points of the trajectory 101 in the distorted space of the voxels. Thus, a cuboid may also be determined in this voxel space that contains or registers this distorted trajectory 101 in full, and simultaneously minimizes the number of voxels to be captured to a limited extent. In most cases, for example, the voxels assigned to the start and end point of the trajectory in the voxel space may be selected as diagonally opposite corner points of the cuboid.

Figure 3:
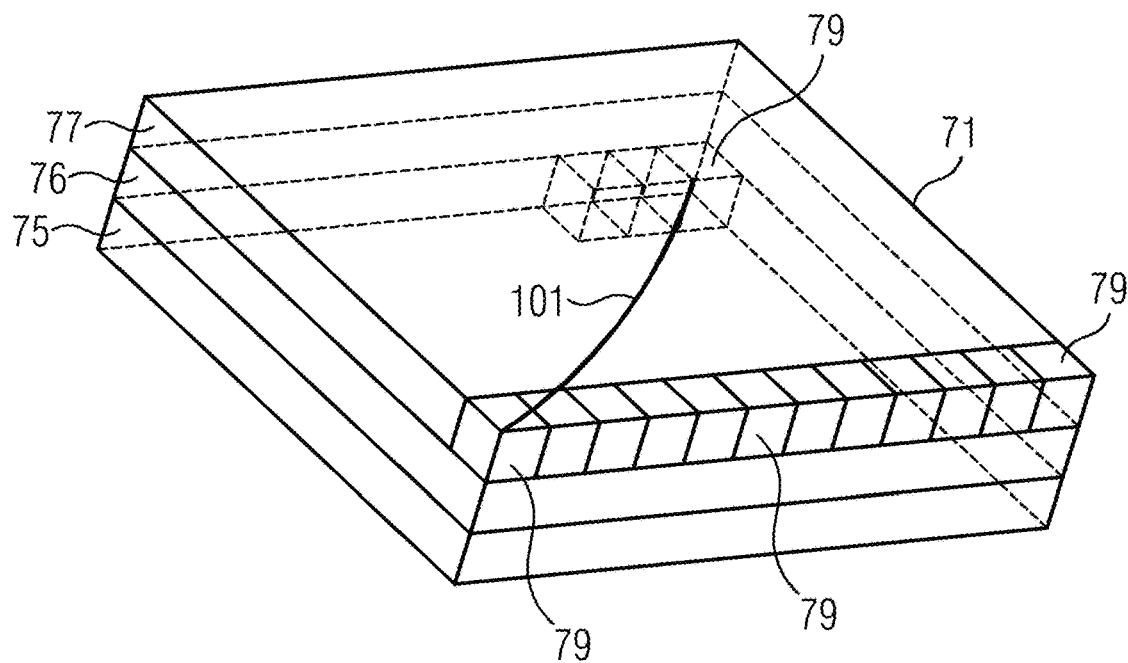
FIG. 3 shows a schematic representation of a slice captured by the magnetic resonance tomography device in the method.

In contrast, FIG. 3 shows an example of a view of the magnetic resonance tomography device. The first slice 71 is defined by a cuboid which has multiple parallel layers 75, 76, 77 composed of voxels in parallel planes. In contrast, the trajectory 101 that is actually straight in the example appears in FIG. 3 as curved.

In this case, it also becomes apparent that it is not possible to capture the trajectory 101 in full because of the curvature with just one layer 75, 76, 77 of voxels, if the voxels have to be small enough to display the trajectory accurately enough for navigation of the medical instrument. The present embodiments therefore also provide a three-dimensional (3D) capture of the first slice 71 with the number of, for example, three layers 75, 76, 77 of voxels. However, because the cuboid is delimited so that the cuboid registers the trajectory in full, the number of voxel values to be captured may be reduced, and thus, the repetition rate may be improved with the same SNR.

The individual layers 75, 76, 77 of the slices 71, 72 may be captured in 3D by phase encoding. The whole slice is excited and its full extent in the FoV is captured with 3D phase encoding in order to prevent aliasing of voxels outside the cuboid. This does increase the number of voxels and thus extends the capture time in the phase encoding. However, this disadvantage is offset by the significantly faster excitation of the slice 71, 72 compared to a selective excitation of the cuboid.

The substantially Cartesian coordinate system shown, even if distorted in the voxel space, is used here merely by way of example and for greater clarity. Because manipulation is intuitive for the user during navigation, the substantially Cartesian coordinate system may be used for the capture of the slices and thus the images generated therefrom. However, the present embodiments may also be applied correspondingly to other coordinate systems.

Figure 4:
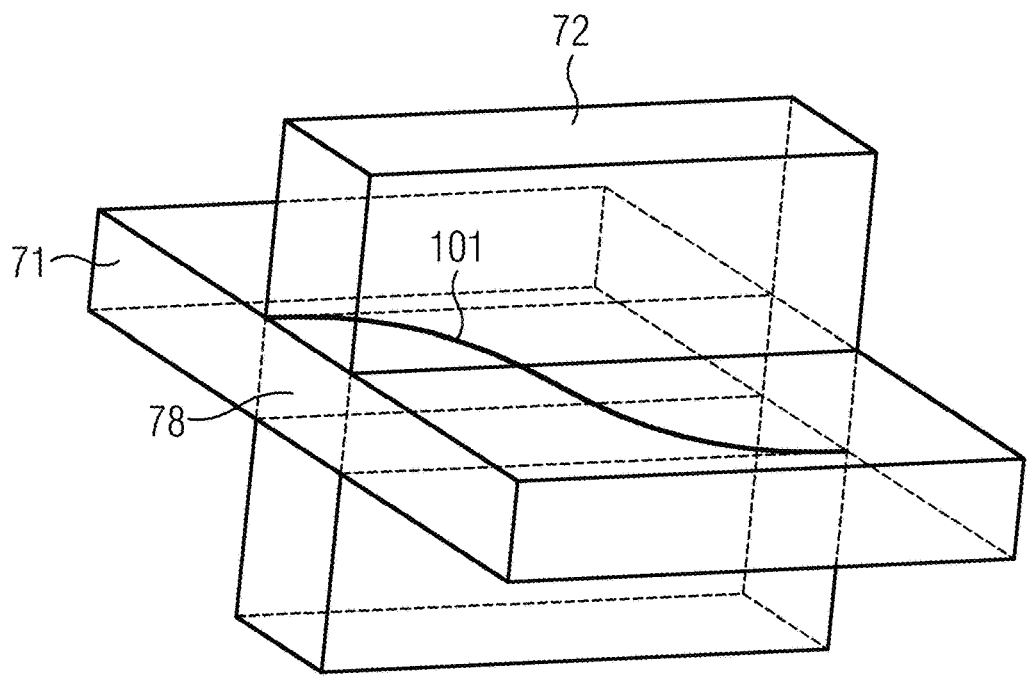
FIG. 4 shows a schematic representation of a relative arrangement of two slices captured by the magnetic resonance tomography device in the method.

FIG. 4 shows a first slice 71 and a second slice 72. The individual layers 75, 76, 77 of the respective slice are no longer shown individually for the sake of clarity. The first slice 71 and the second slice 72 have an intersecting volume 78 that is located inside both slices 71, 72. The first slice 71 and the second slice 72 are arranged at an angle to one another (e.g., normal vectors of the flat surfaces, and thus not the edge surfaces, confine this angle). The angle may be 90 degrees; thus, the first slice 71 may be arranged perpendicularly to the second slice 72. Other angles greater than 30 degrees or 60 degrees may also be provided, so that the slices 71, 72 in each case have a significantly different orientation in respect of the trajectory 101.

The trajectory 101 is registered to this intersecting volume 78, so that the trajectory 101 is also captured in each case both during capture of the first slice 71 and during capture of the second slice 72. In this way, the controller 23 may update a position of the medical instrument 60 along the trajectory 101 in the images from two different perspectives in parallel to the slices 71, 72 at double the frequency.

FIG. 5 shows a schematic flow chart of a, embodiment of the method. The method is executed on a magnetic resonance tomography device 1 of the present embodiments.

In act S20, a first slice 71 is captured by 3D encoding by the magnetic resonance tomography device 1 under the control of the controller 23. The first slice 71 in this case has a plurality of layers 75, 76, 77, in which voxels 79 are arranged. The position (e.g., location and orientation) and the slice thickness of the first slice 71 is in this case selected by the controller 23 as a function of the trajectory 101 as a function of a predetermined distortion of the magnetic resonance tomography device 1 during mapping by the controller 23, such that the trajectory 101 is captured in full by the first slice 71. To this end reference is also made to the explanations for FIG. 2 and FIG. 3.

The predetermined distortion may also be determined beforehand by the controller 23 using a calibration measurement in act S10, for example, with a phantom with a grid composed of MR-active samples at predetermined positions.

In act S30, a second slice 72 is captured by 3D encoding by the magnetic resonance tomography device 1 under the control of the controller 23. The location of the second slice 72 and the slice thickness are likewise selected as a function of the trajectory 101 and as a function of the predetermined distortion of the magnetic resonance tomography device 1, so that the trajectory 101 is captured in full by the second slice 72.

The orientation of the first slice 71 and the second slice 72 relative thereto is, as shown in FIG. 4 and explained in this respect, selected by the controller 23 such that the first slice 71 and the second slice 72 confine an angle greater than 30 degrees or 60 degrees (e.g., equal to 90 degrees), and the trajectory 101 of the medical instrument 60 and/or the medical instrument 60 lies in an intersecting volume 78 of the first slice 71 and the second slice 72.

In act S70, a sequence of two-dimensional images of the medical instrument 60 in a predetermined plane is generated by the controller 23. An intersecting image through the reconstructed voxels 79 of the intersecting volume 78 along this plane or a projection onto this plane may, for example, be provided.

The sequence of images in this case contains images that were generated from the first slice 71 and images that were generated from the second slice 72. The plane of representation of the respective image is in this case substantially parallel to the slice from which the respective image was generated. In one embodiment, the first slice 71 is generated in act S20, alternating with the second slice S72 in act S30. In one embodiment, also in each case, the intersecting image is generated directly from the captured magnetic resonance data of the respective slice 71, 72, before or while the respective other slice 71, 72 is captured. Thus, the images may be generated as promptly as possible. Because, for example, the parts of the images that show the intersecting volume 78 are updated from the captured data or voxels of the first slice 71 and the second slice 72, the representations of the medical engineering instrument may be updated in both the images at double the repetition rate.

In act S80, the two-dimensional images are then each output by the controller 23 to a user (e.g., on a screen 24). The output in this case takes place as promptly as possible after the capture and generation of the image from the respective slice 71, 72. The act sequence may be: capture S20 of a first slice 71; generation S70 of the image of the first slice 71; and immediate output S80 of the image of the first slice; before or while in act S30 the second slice 72 is captured, a two-dimensional image is generated from the second slice 72 in act S70 and is immediately output in act S980. This sequence consisting of capture S20, S30, generation of two-dimensional images S70, and output S80 for a predetermined duration may be repeated for the duration of a control signal, such as, for example, from a foot switch, or for the duration of an intervention.

In one embodiment of the method, in act S40, the captured magnetic resonance data of the first slice 71 or of the second slice 72 is equalized geometrically by the controller. The magnetic resonance tomography device 1 has geometric distortions in the image of captured objects. These distortions may be caused by inhomogeneities in the static B0 field, nonlinearities of the gradient fields, or eddy currents generated by the gradients.

The distortions are characteristic of or predetermined for a respective magnetic resonance tomography device and the sequences used. The distortions may, for example, be determined with a calibration scan, in which a phantom with a grid of MR-active samples is captured at predetermined positions. The deviation of the determined position from the position specified by the grid produces the distortion, which may be specified in the form of a matrix. For the equalization, an inverse function may be determined therefrom in the form of an inverse matrix.

For the equalization in act S40, pixels or voxels may be determined in the spatial domain, for example, from the captured magnetic resonance data of the first slice 71 or the second slice 72 in k-space by image reconstruction (e.g., based on a 3D Fourier transform). The coordinates thereof are, however, subject to the distortions caused by the magnetic resonance tomography device 1 and may be corrected by applying the inverse matrix to the coordinates.

In order that real-time requirements may be better satisfied while tracking the medical instrument 60, the image capture is to take place at a high rate, so that only a little time is available for signal integration, and thus, the SNR is low. This applies, for example, if for a high spatial resolution, a large number of points is to be captured in k-space. However, the SNR may be improved by averaging or binning over multiple pixels or voxels.

However, the equalization of the geometry is again subject to a major error if the underlying voxels in the image space are larger. In one embodiment of the method, the equalization is first executed on data in the image space that has as high a resolution as possible, even if this is noisy. This is done in order to achieve a better spatial correction with a higher resolution even if the data initially does not provide a better representation of the medical instrument 60 for a viewer. In accordance with the embodiment, averaging is then applied to the geometrically equalized voxels or pixels in act S50 in order to improve the SNR. In this case, the spatial density of the pixels may remain unchanged, but binning, in which the spatial resolution is reduced, may also be performed.

In one embodiment of the method, the trajectory 101 and/or the medical instrument 60 itself may be geometrically curved. In other words, the trajectory 101 and/or the medical instrument 60 itself may not to be part of a straight line. From the perspective of the magnetic resonance tomography device 1 or its controller 23, the difference between a curvature of the trajectory due to distortions in the image and a geometric curvature of the trajectory 101 or of the medical instrument 101 is merely that this property is not determined by the magnetic resonance tomography device 1 and the sequence. If the curvature is known, the curvature may be corrected in a separate step, as already explained for the equalization in act S40. A linear mapping in the form of a matrix may, for example, be provided for a linearization of the curvature. In this case, the equalization from act S40 and the linearization may be executed jointly in one step, in that, for example, the inverse matrix described for S40 may be multiplied by the matrix for the linearization and then applied to the coordinates of the pixels or voxels from the MR capture in act S40.

The curvature of the medical instrument 60 or of the trajectory 101 for the controller 23 is a priori not known (e.g., the curvature is not a constant for the respective magnetic resonance tomography device 1 and the sequence).

In order in acts S20 and S30 to determine the thickness and orientation of the first slice 71 and the second slice 72, the trajectory may, for example, be specified externally (e.g., by a treatment plan) and known by a user input or an electronic data transfer of the controller 23.

In one embodiment, the controller 23 may determine the location of the medical instrument, in that, for example, the controller 23 executes a scan and uses segmentation to capture the position and location of the medical instrument 60. In one embodiment, the images of the first slice S20 and/or the second slice in S30 may be used for this in order to adjust the slice thickness and/or location for a subsequent repetition of acts S20 and/or S30.

In one possible embodiment, in act S60, a third slice is acquired in a 3D capture by the controller 23 with the magnetic resonance tomography device 1. The third slice is captured in what is known as a through-plane acquisition (e.g., the trajectory 101 or the medical instrument 60 penetrates the third slice in the direction of the thickness of the slice; substantially in the direction of the surface normal of the slice). For example, the third slice may be arranged orthogonally to the first slice 71 and the second slice 72. The third slice may thus supply a higher-resolution 3D image of the surrounding area of the trajectory 101. The third slice may be captured with a low repetition rate, since a wider surrounding area of the trajectory 101 changes only slightly and is not absolutely necessary for tracking the medical instrument 60 in real time.

In one embodiment, in act S70, during generation of the two-dimensional image, this is executed as a function of the third slice (e.g., for a wider surrounding area of the trajectory 101). For example, organs or vessels may be segmented from the image data of the first slice 71 and second slice 72, and corresponding image data may be overlaid from the image of the third slice.

Although the invention has been illustrated and described in greater detail by the preferred exemplary embodiment, the invention is nevertheless not restricted by the disclosed examples and other variations can be derived therefrom by the person skilled in the art, without departing from the scope of protection of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A magnetic resonance tomography device for mapping a medical instrument on a trajectory in real time, the magnetic resonance tomography device comprising:
   a controller configured to:
   capture a first slice using three-dimensional (3D) encoding, wherein the controller is configured to select a position of the first slice as a function of the trajectory and a slice thickness of the first slice as a function of a predetermined distortion of the magnetic resonance tomography device during mapping, so that the trajectory is captured in full by the first slice;
   capture a second slice using 3D encoding, wherein the controller is configured to select a position of the second slice as a function of the trajectory and a slice thickness of the second slice as a function of the predetermined distortion of the magnetic resonance tomography device during mapping, so that the trajectory is captured in full by the second slice;
   select a position of the first slice and the second slice, such that the first slice and the second slice confine an angle greater than twenty degrees, and the trajectory of the medical instrument, the medical instrument or the trajectory of the medical instrument and the medical instrument lie in an intersecting volume of the first slice and the second slice;
   generate a sequence of two-dimensional images of the medical instrument in a predetermined plane, wherein the sequence includes images that were generated from the first slice and images that were generated from the second slice; and
   output the sequence of two-dimensional images to a user.

2. A method for mapping a medical instrument in real time using a magnetic resonance tomography device on a trajectory, wherein the magnetic resonance tomography device comprises a controller, the method comprising:
   capturing a first slice by the magnetic resonance tomography device using 3D encoding, wherein a position of the first slice is selected by the controller as a function of the trajectory, and a slice thickness of the first slice is selected as a function of a predetermined distortion of the magnetic resonance tomography device during mapping, so that the trajectory is captured in full by the first slice;
   capturing a second slice using 3D encoding by the magnetic resonance tomography device, wherein a position of the second slice is selected by the controller as a function of the trajectory, and a slice thickness of the second slice as a function of the predetermined distortion of the magnetic resonance tomography device during mapping, so that the trajectory is captured in full by the second slice, wherein the position of the first slice and the second slice is selected such that the first slice and the second slice confine an angle greater than twenty degrees, and the trajectory of the medical instrument, the medical instrument, or the trajectory of the medical instrument and the medical instrument lies in an intersecting volume of the first slice and the second slice;
   generating a sequence of two-dimensional images of the medical instrument in a predetermined plane by the controller, wherein the sequence includes images that were generated from the first slice and images that were generated from the second slice; and
   outputting the sequence of two-dimensional images to a user.

3. In a non-transitory computer-readable storage medium that stores instructions executable by one or more processors for mapping a medical instrument in real time using a magnetic resonance tomography device on a trajectory, wherein the magnetic resonance tomography device comprises a controller, the instructions comprising:
   capturing a first slice by the magnetic resonance tomography device using 3D encoding, wherein a position of the first slice is selected by the controller as a function of the trajectory, and a slice thickness of the first slice is selected as a function of a predetermined distortion of the magnetic resonance tomography device during mapping, so that the trajectory is captured in full by the first slice;
   capturing a second slice using 3D encoding by the magnetic resonance tomography device, wherein a position of the second slice is selected by the controller as a function of the trajectory, and a slice thickness of the second slice as a function of the predetermined distortion of the magnetic resonance tomography device during mapping, so that the trajectory is captured in full by the second slice, wherein the position of the first slice and the second slice is selected such that the first slice and the second slice confine an angle greater than twenty degrees, and the trajectory of the medical instrument, the medical instrument, or the trajectory of the medical instrument and the medical instrument lies in an intersecting volume of the first slice and the second slice;
   generating a sequence of two-dimensional images of the medical instrument in a predetermined plane by the controller, wherein the sequence includes images that were generated from the first slice and images that were generated from the second slice; and
   outputting the sequence of two-dimensional images to a user.

4. The magnetic resonance tomography device of claim 1, wherein the controller is further configured to perform an equalization of the predetermined distortion of the first slice, the second slice, or the first slice and the second slice.

5. The magnetic resonance tomography device of claim 1, wherein the controller is further configured to:
   capture a third slice containing the medical instrument with 3D encoding; and generate images as a function of the third slice during generation of the sequence of two-dimensional images.

6. The magnetic resonance tomography device of claim 1, wherein the trajectory is a curved trajectory.

7. The method of claim 2, further comprising performing, by the controller, an equalization of the predetermined distortion of the first slice, the second slice, or the first slice and the second slice.

8. The method of claim 2, further comprising capturing a third slice containing the medical instrument with 3D encoding by the magnetic resonance tomography device, and
wherein the generating of the sequence of two-dimensional images comprises generating images as a function of the third slice.

9. The method of claim 2, wherein the trajectory is a curved trajectory.

10. The magnetic resonance tomography device of claim 4, wherein the controller is further configured to perform averaging of the first slice, the second slice, or the first slice and the second slice after the equalization.

11. The magnetic resonance tomography device of claim 6, wherein the controller is further configured to perform a linearization of the curved trajectory during generation of the two-dimensional images.

12. The method of claim 7, further comprising performing, by the controller, an averaging of the first slice, the second slice, or the first slice and the second slice after the equalization.

13. The method of claim 9, wherein generating the sequence of the two-dimensional images comprises linearizing the curved trajectory.

14. The magnetic resonance tomography device of claim 10, wherein the controller is further configured to perform the equalization with a resolution greater than a resolution of the two-dimensional images.

15. The method of claim 12, wherein the equalization takes place with a resolution greater than a resolution of the two-dimensional images.

\* \* \* \* \*